United States Patent [19]
Tsien et al.

[11] Patent Number: 6,140,132
[45] Date of Patent: Oct. 31, 2000

[54] FLUORESCENT PROTEIN SENSORS FOR MEASURING THE PH OF A BIOLOGICAL SAMPLE

[75] Inventors: Roger Y. Tsien, La Jolla; Atsushi Miyawaki; Juan Llopis, both of San Diego, all of Calif.

[73] Assignee: The Regents of the University of California, Oakland, Calif.

[21] Appl. No.: 09/094,359

[22] Filed: Jun. 9, 1998

[51] Int. Cl.[7] .......................... G01N 33/52; C07K 14/435
[52] U.S. Cl. .............................................. 436/86; 530/350
[58] Field of Search ................................ 436/86; 530/350

[56] References Cited

PUBLICATIONS

Llopis et al. (Jun. 9, 1998) Proc. Natl. Acad. Sci. USA, vol. 95, pp. 6803–6808.

Kneen et al. (Mar. 1998) Biophysical J., vol. 74, pp. 1591–1599 (abstract).

Guttenplan et al. (1973) BBA, vol. 322, pp. 294–300 (abstract).0.

*Primary Examiner*—Elizabeth Slobodyansky
*Attorney, Agent, or Firm*—Gray Cary Ware & Freidenrich LLP; Lisa A. Haile

[57] ABSTRACT

Disclosed are fluorescent protein sensors for measuring the pH of a sample, nucleic acids encoding them, and methods of use. The preferred fluorescent protein sensors are variants of the green fluorescent protein (GFP) from *Aequorea victoria*. Also disclosed are compositions and methods for measuring the pH of a specific region of a cell, such as the mitochondrial matrix or the Golgi lumen.

16 Claims, 2 Drawing Sheets

SEQUENCE LISTING

<160> NUMBER OF SEQ ID NOS: 18

<210> SEQ ID NO 1
<211> LENGTH: 716
<212> TYPE: DNA
<213> ORGANISM: Aequorea victoria

```
<220> FEATURE:
<221> NAME/KEY: CDS
<222> LOCATION: (1)...(714)
<223> OTHER INFORMATION: Green fluorescent protein

<400> SEQUENCE: 1 atg agt aaa gga gaa gaa ctt ttc act gga gtt gtc cca att ctt gtt        48
Met Ser Lys Gly Glu Glu Leu Phe Thr Gly Val Val Pro Ile Leu Val
 1               5                  10                  15 gaa tta gat ggt gat gtt aat ggg cac aaa ttt tct gtc agt gga gag        96
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tgc       144
Gly Glu Gly Asp Ala Thr Tyr Gly Lys Leu Thr Leu Lys Phe Ile Cys
        35                  40                  45 act act gga aaa cta cct gtt cca tgg cca aca ctt gtc act act ttc       192
Thr Thr Gly Lys Leu Pro Val Pro Trp Pro Thr Leu Val Thr Thr Phe
 50                  55                  60 tct tat ggt gtt caa tgc ttt tca aga tac cca gat cat atg aaa cgg       240
Ser Tyr Gly Val Gln Cys Phe Ser Arg Tyr Pro Asp His Met Lys Arg
 65                  70                  75                  80 cat gac ttt ttc aag agt gcc atg ccc gaa ggt tat gta cag gaa aga       288
His Asp Phe Phe Lys Ser Ala Met Pro Glu Gly Tyr Val Gln Glu Arg
                85                  90                  95 act ata ttt ttc aaa gat gac ggg aac tac aag aca cgt gct gaa gtc       336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att       384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac       432
Asp Phe Lys Glu Asp Gly Asn Ile Leu Gly His Lys Leu Glu Tyr Asn
130                 135                 140 tat aac tca cac aat gta tac atc atg gca gac aaa caa aag aat gga       480
Tyr Asn Ser His Asn Val Tyr Ile Met Ala Asp Lys Gln Lys Asn Gly
145                 150                 155                 160 atc aaa gtt aac ttc aaa att aga cac aac att gaa gat gga agc gtt       528
Ile Lys Val Asn Phe Lys Ile Arg His Asn Ile Glu Asp Gly Ser Val
                165                 170                 175 caa cta gca gac cat tat caa caa aat act cca att ggc gat ggc cct       576
Gln Leu Ala Asp His Tyr Gln Gln Asn Thr Pro Ile Gly Asp Gly Pro
            180                 185                 190 gtc ctt tta cca gac aac cat tac ctg tcc aca caa tct gcc ctt tcg       624
Val Leu Leu Pro Asp Asn His Tyr Leu Ser Thr Gln Ser Ala Leu Ser
        195                 200                 205 aaa gat ccc aac gaa aag aga gac cac atg gtc ctt ctt gag ttt gta       672
Lys Asp Pro Asn Glu Lys Arg Asp His Met Val Leu Leu Glu Phe Val
    210                 215                 220 aca gct gct ggg att aca cat ggc atg gat gaa cta tac aaa              714
Thr Ala Ala Gly Ile Thr His Gly Met Asp Glu Leu Tyr Lys
225                 230                 235 ta                                                                    716

<210> SEQ ID NO 2
<211> LENGTH: 238
<212> TYPE: PRT
<213> ORGANISM: Aequorea victoria

<400> SEQUENCE: 2

Met Ser Lys Gly Glu Glu Leu Phe Thr Gly Val Val Pro Ile Leu Val
 1               5                  10                  15
```

```
Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
             85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
        180                 185                 190

Val Leu Leu Pro Asp Asn His Tyr Leu Ser Thr Gln Ser Ala Leu Ser
    195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 3
<211> LENGTH: 720
<212> TYPE: DNA
<213> ORGANISM: Aequorea victoria
<220> FEATURE:
<221> NAME/KEY: CDS
<222> LOCATION: (1)...(717)
<223> OTHER INFORMATION: EGFP

<400> SEQUENCE: 3 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
  1               5                  10                  15 gtc gag ctg gac ggc gac gta aac ggc cac agg ttc agc gtg tcc ggc      96
Val Glu Leu Asp Gly Asp Val Asn Gly His Arg Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
             85                  90                  95
```

```
cgc acc atc ttc ttc aag gac gac ggc aac tac aag acc cgc gcc gag        336
Arg Thr Ile Phe Phe Lys Asp Asp Gly Asn Tyr Lys Thr Arg Ala Glu
        100                 105                 110 gtg aag ttc gag ggc gac acc ctg gtg aac cgc atc gag ctg aag ggc        384
Val Lys Phe Glu Gly Asp Thr Leu Val Asn Arg Ile Glu Leu Lys Gly
    115                 120                 125 atc gac ttc aag gag gac ggc aac atc ctg ggg cac aag ctg gag tac        432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac        480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc        528
Gly Ile Lys Val Asn Phe Lys Ile Arg His Asn Ile Glu Asp Gly Ser
            165                 170                 175 gtg cag ctc gcc gac cac tac cag cag aac acc ccc atc ggc gac ggc        576
Val Gln Leu Ala Asp His Tyr Gln Gln Asn Thr Pro Ile Gly Asp Gly
        180                 185                 190 ccc gtg ctg ctg ccc gac aac cac tac ctg agc acc cag tcc gcc ctg        624
Pro Val Leu Leu Pro Asp Asn His Tyr Leu Ser Thr Gln Ser Ala Leu
    195                 200                 205 agc aaa gac ccc aac gag aag cgc gat cac atg gtc ctg ctg gag ttc        672
Ser Lys Asp Pro Asn Glu Lys Arg Asp His Met Val Leu Leu Glu Phe
210                 215                 220 gtg acc gcc gcc ggg atc act ctc ggc atg gac gag ctg tac aag            717
Val Thr Ala Ala Gly Ile Thr Leu Gly Met Asp Glu Leu Tyr Lys
225                 230                 235 taa                                                                    720

<210> SEQ ID NO 4
<211> LENGTH: 239
<212> TYPE: PRT
<213> ORGANISM: Aequorea victoria

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

```
Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 5
<211> LENGTH: 720
<212> TYPE: DNA
<213> ORGANISM: Aequorea victoria
<220> FEATURE:
<221> NAME/KEY: CDS
<222> LOCATION: (1)...(717)
<223> OTHER INFORMATION: EYFP

<400> SEQUENCE: 5 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
  1               5                  10                  15 gtc gag ctg gac ggc gac gta aac ggc cac agg ttc agc gtg tcc ggc      96
Val Glu Leu Asp Gly Asp Val Asn Gly His Arg Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50                  55                  60 ttc ggc tac ggc gtg cag tgc ttc gcc cgc tac ccc gac cac atg aag     240
Phe Gly Tyr Gly Val Gln Cys Phe Ala Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg     624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
    210                 215                 220
```

```
gtg acc gcc gcc ggg atc act ctc ggc atg gac gag ctg tac aag       717
Val Thr Ala Ala Gly Ile Thr Leu Gly Met Asp Glu Leu Tyr Lys
225                 230                 235 taa                                                               720
```

<210> SEQ ID NO 6
<211> LENGTH: 239
<212> TYPE: PRT
<213> ORGANISM: Aequorea victoria

<400> SEQUENCE: 6

```
Met Val Ser Lys Gly Glu Glu Leu Phe Thr Gly Val Val Pro Ile Leu
 1               5                  10                  15

Val Glu Leu Asp Gly Asp Val Asn Gly His Arg Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 7
<211> LENGTH: 720
<212> TYPE: DNA
<213> ORGANISM: Aequorea victoria
<220> FEATURE:
<221> NAME/KEY: CDS
<222> LOCATION: (1)...(717)
<223> OTHER INFORMATION: ECFP

<400> SEQUENCE: 7

```
atg gtg agc aag ggc gag gag ctg ttc acc ggg gtg gtg ccc atc ctg    48
Met Val Ser Lys Gly Glu Glu Leu Phe Thr Gly Val Val Pro Ile Leu
 1               5                  10                  15 gtc gag ctg gac ggc gac gta aac ggc cac agg ttc agc gtg tcc ggc    96
Val Glu Leu Asp Gly Asp Val Asn Gly His Arg Phe Ser Val Ser Gly
             20                  25                  30
```

```
gag ggc gag ggc gat gcc acc tac ggc aag ctg acc ctg aag ttc atc    144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc    192
Cys Thr Thr Gly Lys Leu Pro Val Pro Trp Pro Thr Leu Val Thr Thr
 50                  55                  60 ctg acc tgg ggc gtg cag tgc ttc agc cgc tac ccc gac cac atg aag    240
Leu Thr Trp Gly Val Gln Cys Phe Ser Arg Tyr Pro Asp His Met Lys
 65                  70                  75                  80 cag cac gac ttc ttc aag tcc gcc atg ccc gaa ggc tac gtc cag gag    288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag    336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc    384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac    432
Ile Asp Phe Lys Glu Asp Gly Asn Ile Leu Gly His Lys Leu Glu Tyr
    130                 135                 140 aac tac atc agc cac aac gtc tat atc acc gcc gac aag cag aag aac    480
Asn Tyr Ile Ser His Asn Val Tyr Ile Thr Ala Asp Lys Gln Lys Asn
145                 150                 155                 160 ggc atc aag gcc cac ttc aag atc cgc cac aac atc gag gac ggc agc    528
Gly Ile Lys Ala His Phe Lys Ile Arg His Asn Ile Glu Asp Gly Ser
                165                 170                 175 gtg cag ctc gcc gac cac tac cag cag aac acc ccc atc ggc gac ggc    576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg    624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc    672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag         717
Val Thr Ala Ala Gly Ile Thr Leu Gly Met Asp Glu Leu Tyr Lys
225                 230                 235 taa                                                                 720
```

<210> SEQ ID NO 8
<211> LENGTH: 239
<212> TYPE: PRT
<213> ORGANISM: Aequorea victoria

<400> SEQUENCE: 8

```
Met Val Ser Lys Gly Glu Glu Leu Phe Thr Gly Val Val Pro Ile Leu
 1               5                  10                  15

Val Glu Leu Asp Gly Asp Val Asn Gly His Arg Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
```

```
                        85                  90                  95
Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 9
<211> LENGTH: 720
<212> TYPE: DNA
<213> ORGANISM: Aequorea victoria
<220> FEATURE:
<221> NAME/KEY: CDS
<222> LOCATION: (1)...(717)
<223> OTHER INFORMATION: EYFP-V68L/Q69K

<400> SEQUENCE: 9
```

| | | | | | | | | | | | | | | | | |
|---|---|---|---|---|---|---|---|---|---|---|---|---|---|---|---|---|
| atg | gtg | agc | aag | ggc | gag | gag | ctg | ttc | acc | ggg | gtg | gtg | ccc | atc | ctg | 48 |
| Met | Val | Ser | Lys | Gly | Glu | Glu | Leu | Phe | Thr | Gly | Val | Val | Pro | Ile | Leu | |
| 1 | | | | 5 | | | | | 10 | | | | | 15 | | |
| gtc | gag | ctg | gac | ggc | gac | gta | aac | ggc | cac | agg | ttc | agc | gtg | tcc | ggc | 96 |
| Val | Glu | Leu | Asp | Gly | Asp | Val | Asn | Gly | His | Arg | Phe | Ser | Val | Ser | Gly | |
| | | | 20 | | | | | 25 | | | | | 30 | | | |
| gag | ggc | gag | ggc | gat | gcc | acc | tac | ggc | aag | ctg | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
| | | 35 | | | | | 40 | | | | | 45 | | | | |
| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| | 50 | | | | | 55 | | | | | 60 | | | | | |
| ttc | ggc | tac | ggc | ctg | aag | tgc | ttc | gcc | cgc | tac | ccc | gac | cac | atg | aag | 240 |
| Phe | Gly | Tyr | Gly | Leu | Lys | Cys | Phe | Ala | Arg | Tyr | Pro | Asp | His | Met | Lys | |
| 65 | | | | | 70 | | | | | 75 | | | | | 80 | |
| cag | cac | gac | ttc | ttc | aag | tcc | gcc | atg | ccc | gaa | ggc | tac | gtc | cag | gag | 288 |
| Gln | His | Asp | Phe | Phe | Lys | Ser | Ala | Met | Pro | Glu | Gly | Tyr | Val | Gln | Glu | |
| | | | | 85 | | | | | 90 | | | | | 95 | | |
| cgc | acc | atc | ttc | ttc | aag | gac | gac | ggc | aac | tac | aag | acc | cgc | gcc | gag | 336 |
| Arg | Thr | Ile | Phe | Phe | Lys | Asp | Asp | Gly | Asn | Tyr | Lys | Thr | Arg | Ala | Glu | |
| | | | | 100 | | | | | 105 | | | | | 110 | | |
| gtg | aag | ttc | gag | ggc | gac | acc | ctg | gtg | aac | cgc | atc | gag | ctg | aag | ggc | 384 |
| Val | Lys | Phe | Glu | Gly | Asp | Thr | Leu | Val | Asn | Arg | Ile | Glu | Leu | Lys | Gly | |
| | | | 115 | | | | | 120 | | | | | 125 | | | |
| atc | gac | ttc | aag | gag | gac | ggc | aac | atc | ctg | ggg | cac | aag | ctg | gag | tac | 432 |
| Ile | Asp | Phe | Lys | Glu | Asp | Gly | Asn | Ile | Leu | Gly | His | Lys | Leu | Glu | Tyr | |
| | | 130 | | | | | 135 | | | | | 140 | | | | |
| aac | tac | aac | agc | cac | aac | gtc | tat | atc | atg | gcc | gac | aag | cag | aag | aac | 480 |
| Asn | Tyr | Asn | Ser | His | Asn | Val | Tyr | Ile | Met | Ala | Asp | Lys | Gln | Lys | Asn | |

```
                                                                        145                     150                     155                     160 ggc atc aag gtg aac ttc aag atc cgc cac aac atc gag gac ggc agc         528
Gly Ile Lys Val Asn Phe Lys Ile Arg His Asn Ile Glu Asp Gly Ser
                    165                     170                     175 gtg cag ctc gcc gac cac tac cag cag aac acc ccc atc ggc gac ggc         576
Val Gln Leu Ala Asp His Tyr Gln Gln Asn Thr Pro Ile Gly Asp Gly
        180                     185                     190 ccc gtg ctg ctg ccc gac aac cac tac ctg agc tac cag tcc gcc ctg         624
Pro Val Leu Leu Pro Asp Asn His Tyr Leu Ser Tyr Gln Ser Ala Leu
            195                     200                     205 agc aaa gac ccc aac gag aag cgc gat cac atg gtc ctg ctg gag ttc         672
Ser Lys Asp Pro Asn Glu Lys Arg Asp His Met Val Leu Leu Glu Phe
    210                     215                     220 gtg acc gcc gcc ggg atc act ctc ggc atg gac gag ctg tac aag             717
Val Thr Ala Ala Gly Ile Thr Leu Gly Met Asp Glu Leu Tyr Lys
225                     230                     235 taa                                                                     720

<210> SEQ ID NO 10
<211> LENGTH: 239
<212> TYPE: PRT
<213> ORGANISM: Aequorea victoria

<400> SEQUENCE: 10

Met Val Ser Lys Gly Glu Glu Leu Phe Thr Gly Val Val Pro Ile Leu
  1               5                  10                  15

Val Glu Leu Asp Gly Asp Val Asn Gly His Arg Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Lys Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 11
```

```
<211> LENGTH: 768
<212> TYPE: DNA
<213> ORGANISM: Aequorea victoria
<220> FEATURE:
<221> NAME/KEY: CDS
<222> LOCATION: (1)...(765)
<223> OTHER INFORMATION: ECFP-mito

<400> SEQUENCE: 11 atg ctg agc ctg cgc cag agc atc cgc ttc ttc aag cgc agc ggc atc      48
Met Leu Ser Leu Arg Gln Ser Ile Arg Phe Phe Lys Arg Ser Gly Ile
 1               5                  10                  15 atg gtg agc aag ggc gag gag ctg ttc acc ggg gtg gtg ccc atc ctg      96
Met Val Ser Lys Gly Glu Glu Leu Phe Thr Gly Val Val Pro Ile Leu
                20                  25                  30 gtc gag ctg gac ggc gac gta aac ggc cac agg ttc agc gtg tcc ggc     144
Val Glu Leu Asp Gly Asp Val Asn Gly His Arg Phe Ser Val Ser Gly
         35                  40                  45 gag ggc gag ggc gat gcc acc tac ggc aag ctg acc ctg aag ttc atc     192
Glu Gly Glu Gly Asp Ala Thr Tyr Gly Lys Leu Thr Leu Lys Phe Ile
     50                  55                  60 tgc acc acc ggc aag ctg ccc gtg ccc tgg ccc acc ctc gtg acc acc     240
Cys Thr Thr Gly Lys Leu Pro Val Pro Trp Pro Thr Leu Val Thr Thr
 65                  70                  75                  80 ctg acc tgg ggc gtg cag tgc ttc agc cgc tac ccc gac cac atg aag     288
Leu Thr Trp Gly Val Gln Cys Phe Ser Arg Tyr Pro Asp His Met Lys
                 85                  90                  95 cag cac gac ttc ttc aag tcc gcc atg ccc gaa ggc tac gtc cag gag     336
Gln His Asp Phe Phe Lys Ser Ala Met Pro Glu Gly Tyr Val Gln Glu
                100                 105                 110 cgc acc atc ttc ttc aag gac gac ggc aac tac aag acc cgc gcc gag     384
Arg Thr Ile Phe Phe Lys Asp Asp Gly Asn Tyr Lys Thr Arg Ala Glu
            115                 120                 125 gtg aag ttc gag ggc gac acc ctg gtg aac cgc atc gag ctg aag ggc     432
Val Lys Phe Glu Gly Asp Thr Leu Val Asn Arg Ile Glu Leu Lys Gly
        130                 135                 140 atc gac ttc aag gag gac ggc aac atc ctg ggg cac aag ctg gag tac     480
Ile Asp Phe Lys Glu Asp Gly Asn Ile Leu Gly His Lys Leu Glu Tyr
145                 150                 155                 160 aac tac atc agc cac aac gtc tat atc acc gcc gac aag cag aag aac     528
Asn Tyr Ile Ser His Asn Val Tyr Ile Thr Ala Asp Lys Gln Lys Asn
                165                 170                 175 ggc atc aag gcc cac ttc aag atc cgc cac aac atc gag gac ggc agc     576
Gly Ile Lys Ala His Phe Lys Ile Arg His Asn Ile Glu Asp Gly Ser
            180                 185                 190 gtg cag ctc gcc gac cac tac cag cag aac acc ccc atc ggc gac ggc     624
Val Gln Leu Ala Asp His Tyr Gln Gln Asn Thr Pro Ile Gly Asp Gly
        195                 200                 205 ccc gtg ctg ctg ccc gac aac cac tac ctg agc acc cag tcc gcc ctg     672
Pro Val Leu Leu Pro Asp Asn His Tyr Leu Ser Thr Gln Ser Ala Leu
    210                 215                 220 agc aaa gac ccc aac gag aag cgc gat cac atg gtc ctg ctg gag ttc     720
Ser Lys Asp Pro Asn Glu Lys Arg Asp His Met Val Leu Leu Glu Phe
225                 230                 235                 240 gtg acc gcc gcc ggg atc act ctc ggc atg gac gag ctg tac aag          765
Val Thr Ala Ala Gly Ile Thr Leu Gly Met Asp Glu Leu Tyr Lys
                245                 250                 255 taa                                                                  768

<210> SEQ ID NO 12
<211> LENGTH: 255
```

```
<212> TYPE: PRT
<213> ORGANISM: Aequorea victoria

<400> SEQUENCE: 12

Met Leu Ser Leu Arg Gln Ser Ile Arg Phe Phe Lys Arg Ser Gly Ile
 1               5                  10                  15

Met Val Ser Lys Gly Glu Glu Leu Phe Thr Gly Val Val Pro Ile Leu
            20                  25                  30

Val Glu Leu Asp Gly Asp Val Asn Gly His Arg Phe Ser Val Ser Gly
        35                  40                  45

Glu Gly Glu Gly Asp Ala Thr Tyr Gly Lys Leu Thr Leu Lys Phe Ile
    50                  55                  60

Cys Thr Thr Gly Lys Leu Pro Val Pro Trp Pro Thr Leu Val Thr Thr
65                  70                  75                  80

Leu Thr Trp Gly Val Gln Cys Phe Ser Arg Tyr Pro Asp His Met Lys
                85                  90                  95

Gln His Asp Phe Phe Lys Ser Ala Met Pro Glu Gly Tyr Val Gln Glu
            100                 105                 110

Arg Thr Ile Phe Phe Lys Asp Asp Gly Asn Tyr Lys Thr Arg Ala Glu
        115                 120                 125

Val Lys Phe Glu Gly Asp Thr Leu Val Asn Arg Ile Glu Leu Lys Gly
    130                 135                 140

Ile Asp Phe Lys Glu Asp Gly Asn Ile Leu Gly His Lys Leu Glu Tyr
145                 150                 155                 160

Asn Tyr Ile Ser His Asn Val Tyr Ile Thr Ala Asp Lys Gln Lys Asn
                165                 170                 175

Gly Ile Lys Ala His Phe Lys Ile Arg His Asn Ile Glu Asp Gly Ser
            180                 185                 190

Val Gln Leu Ala Asp His Tyr Gln Gln Asn Thr Pro Ile Gly Asp Gly
        195                 200                 205

Pro Val Leu Leu Pro Asp Asn His Tyr Leu Ser Thr Gln Ser Ala Leu
    210                 215                 220

Ser Lys Asp Pro Asn Glu Lys Arg Asp His Met Val Leu Leu Glu Phe
225                 230                 235                 240

Val Thr Ala Ala Gly Ile Thr Leu Gly Met Asp Glu Leu Tyr Lys
                245                 250                 255

<210> SEQ ID NO 13
<211> LENGTH: 768
<212> TYPE: DNA
<213> ORGANISM: Aequorea victoria
<220> FEATURE:
<221> NAME/KEY: CDS
<222> LOCATION: (1)...(765)
<223> OTHER INFORMATION: EYFP-mito

<400> SEQUENCE: 13 atg ctg agc ctg cgc cag agc atc cgc ttc ttc aag cgc agc ggc atc    48
Met Leu Ser Leu Arg Gln Ser Ile Arg Phe Phe Lys Arg Ser Gly Ile
 1               5                  10                  15 atg gtg agc aag ggc gag gag ctg ttc acc ggg gtg gtg ccc atc ctg    96
Met Val Ser Lys Gly Glu Glu Leu Phe Thr Gly Val Val Pro Ile Leu
            20                  25                  30 gtc gag ctg gac ggc gac gta aac ggc cac agg ttc agc gtg tcc ggc   144
Val Glu Leu Asp Gly Asp Val Asn Gly His Arg Phe Ser Val Ser Gly
        35                  40                  45 gag ggc gag ggc gat gcc acc tac ggc aag ctg acc ctg aag ttc atc   192
Glu Gly Glu Gly Asp Ala Thr Tyr Gly Lys Leu Thr Leu Lys Phe Ile
```

-continued

```
             50                  55                  60
tgc acc acc ggc aag ctg ccc gtg ccc tgg ccc acc ctc gtg acc acc         240
Cys Thr Thr Gly Lys Leu Pro Val Pro Trp Pro Thr Leu Val Thr Thr
 65                  70                  75                  80 ttc ggc tac ggc gtg cag tgc ttc gcc cgc tac ccc gac cac atg aag         288
Phe Gly Tyr Gly Val Gln Cys Phe Ala Arg Tyr Pro Asp His Met Lys
                 85                  90                  95 cag cac gac ttc ttc aag tcc gcc atg ccc gaa ggc tac gtc cag gag         336
Gln His Asp Phe Phe Lys Ser Ala Met Pro Glu Gly Tyr Val Gln Glu
                100                 105                 110 cgc acc atc ttc ttc aag gac gac ggc aac tac aag acc cgc gcc gag         384
Arg Thr Ile Phe Phe Lys Asp Asp Gly Asn Tyr Lys Thr Arg Ala Glu
            115                 120                 125 gtg aag ttc gag ggc gac acc ctg gtg aac cgc atc gag ctg aag ggc         432
Val Lys Phe Glu Gly Asp Thr Leu Val Asn Arg Ile Glu Leu Lys Gly
        130                 135                 140 atc gac ttc aag gag gac ggc aac atc ctg ggg cac aag ctg gag tac         480
Ile Asp Phe Lys Glu Asp Gly Asn Ile Leu Gly His Lys Leu Glu Tyr
145                 150                 155                 160 aac tac aac agc cac aac gtc tat atc atg gcc gac aag cag aag aac         528
Asn Tyr Asn Ser His Asn Val Tyr Ile Met Ala Asp Lys Gln Lys Asn
                165                 170                 175 ggc atc aag gtg aac ttc aag atc cgc cac aac atc gag gac ggc agc         576
Gly Ile Lys Val Asn Phe Lys Ile Arg His Asn Ile Glu Asp Gly Ser
            180                 185                 190 gtg cag ctc gcc gac cac tac cag cag aac acc ccc atc ggc gac ggc         624
Val Gln Leu Ala Asp His Tyr Gln Gln Asn Thr Pro Ile Gly Asp Gly
        195                 200                 205 ccc gtg ctg ctg ccc gac aac cac tac ctg agc tac cag tcc gcc ctg         672
Pro Val Leu Leu Pro Asp Asn His Tyr Leu Ser Tyr Gln Ser Ala Leu
    210                 215                 220 agc aaa gac ccc aac gag aag cgc gat cac atg gtc ctg ctg gag ttc         720
Ser Lys Asp Pro Asn Glu Lys Arg Asp His Met Val Leu Leu Glu Phe
225                 230                 235                 240 gtg acc gcc gcc ggg atc act ctc ggc atg gac gag ctg tac aag             765
Val Thr Ala Ala Gly Ile Thr Leu Gly Met Asp Glu Leu Tyr Lys
                245                 250                 255 taa                                                                     768
```

<210> SEQ ID NO 14
<211> LENGTH: 255
<212> TYPE: PRT
<213> ORGANISM: Aequorea victoria

<400> SEQUENCE: 14

```
Met Leu Ser Leu Arg Gln Ser Ile Arg Phe Phe Lys Arg Ser Gly Ile
 1               5                  10                  15

Met Val Ser Lys Gly Glu Glu Leu Phe Thr Gly Val Val Pro Ile Leu
                20                  25                  30

Val Glu Leu Asp Gly Asp Val Asn Gly His Arg Phe Ser Val Ser Gly
            35                  40                  45

Glu Gly Glu Gly Asp Ala Thr Tyr Gly Lys Leu Thr Leu Lys Phe Ile
        50                  55                  60

Cys Thr Thr Gly Lys Leu Pro Val Pro Trp Pro Thr Leu Val Thr Thr
 65                  70                  75                  80

Phe Gly Tyr Gly Val Gln Cys Phe Ala Arg Tyr Pro Asp His Met Lys
                 85                  90                  95

Gln His Asp Phe Phe Lys Ser Ala Met Pro Glu Gly Tyr Val Gln Glu
```

```
                100                 105                 110
Arg Thr Ile Phe Phe Lys Asp Asp Gly Asn Tyr Lys Thr Arg Ala Glu
            115                 120                 125

Val Lys Phe Glu Gly Asp Thr Leu Val Asn Arg Ile Glu Leu Lys Gly
            130                 135                 140

Ile Asp Phe Lys Glu Asp Gly Asn Ile Leu Gly His Lys Leu Glu Tyr
145                 150                 155                 160

Asn Tyr Asn Ser His Asn Val Tyr Ile Met Ala Asp Lys Gln Lys Asn
                165                 170                 175

Gly Ile Lys Val Asn Phe Lys Ile Arg His Asn Ile Glu Asp Gly Ser
            180                 185                 190

Val Gln Leu Ala Asp His Tyr Gln Gln Asn Thr Pro Ile Gly Asp Gly
            195                 200                 205

Pro Val Leu Leu Pro Asp Asn His Tyr Leu Ser Tyr Gln Ser Ala Leu
            210                 215                 220

Ser Lys Asp Pro Asn Glu Lys Arg Asp His Met Val Leu Leu Glu Phe
225                 230                 235                 240

Val Thr Ala Ala Gly Ile Thr Leu Gly Met Asp Glu Leu Tyr Lys
                245                 250                 255

<210> SEQ ID NO 15
<211> LENGTH: 5
<212> TYPE: PRT
<213> ORGANISM: Homo sapiens

<400> SEQUENCE: 15

Lys Lys Lys Arg Lys
1               5

<210> SEQ ID NO 16
<211> LENGTH: 26
<212> TYPE: PRT
<213> ORGANISM: Homo sapiens

<400> SEQUENCE: 16

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 17
<211> LENGTH: 4
<212> TYPE: PRT
<213> ORGANISM: Homo sapiens

<400> SEQUENCE: 17

Lys Asp Glu Leu
1

<210> SEQ ID NO 18
<211> LENGTH: 4
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: Linker sequence

<400> SEQUENCE: 18

Arg Ser Gly Ile
```

FLUORESCENT PROTEIN SENSORS FOR MEASURING THE PH OF A BIOLOGICAL SAMPLE

STATEMENT AS TO FEDERALLY SPONSORED RESEARCH

This invention was made with Government support under Grant No. NS27177, awarded by the National Institutes of Health. The Government may have rights in this invention.

FIELD OF THE INVENTION

The invention relates generally to compositions and methods for measuring the pH of a sample and more particularly to fluorescent protein sensors for measuring the pH of a biological sample.

BACKGROUND OF THE INVENTION

The pH within various cellular compartments is regulated to provide for the optimal activity of many cellular processes. In the secretory pathway, posttranslational processing of secretory proteins, the cleavage of prohormones, and the retrieval of escaped luminal endoplasmic reticulum proteins are all pH-dependent.

Several techniques have been described for measuring intracellular pH. Commonly used synthetic pH indicators can be localized to the cytosol and nucleus, but not selectively in organelles other than those in the endocytotic pathway. In addition, some cells are resistant to loading with cell-permeant dyes because of physical barriers such as the cell wall in bacteria, yeast, and plants, or the thickness of a tissue preparation such as brain slices.

Several methods have been described for measuring pH in specific regions of the cell. One technique uses microinjection of fluorescent indicators enclosed in liposomes. Once inside the cell, the liposomes fuse with vesicles in the trans-Golgi, and the pH of the intracellular compartments is determined by observing the fluorescence of the indicator. This procedure can be laborious, and the fluorescence of the indicator can be diminished due to leakage of the fluorescent indicator from the Golgi, or flux of the fluorescent indicator out of the Golgi as part of the secretory traffic in the Golgi pathway. In addition, the fusion of the liposomes and components of the Golgi must take place at 37° C.; however, this temperature facilitates leakage and flux of the fluorescent indicator from the Golgi.

A second method for measuring pH utilizes retrograde transport of fluorescein-labeled verotoxin 1B, which stains the entire Golgi complex en route to the endoplasmic reticulum. This method can be used, however, only in cells bearing the receptor globotriaosyl ceramide on the plasma membrane, and it may be limited by the residence time of the verotoxin in transit through the Golgi.

In a third method, intracellular pH has been measured using the chimeric protein CD25-TGN38, which cycles between the trans-Golgi network and the plasma membrane. At the plasma membrane, the CD25-motif binds extracellular anti-CD25 antibodies conjugated with a pH-sensitive fluorophore. Measurement of fluorescence upon return of the bound complex to the Golgi can be used to measure the pH of the organelle.

SUMMARY OF THE INVENTION

The invention is based on the discovery that proteins derived from the *Aequorea victoria* green fluorescent protein (GFP) show reversible changes in fluorescence over physiological pH ranges.

Accordingly, in one aspect, the invention provides a method for determining the pH of a sample by contacting the sample with an indicator including a first fluorescent protein moiety whose emission intensity changes as the pH varies between 5 and 10, exciting the indicator, and the determining the intensity at a first wavelength. The emission intensity of the first fluorescent protein moiety indicates the pH of the sample.

In another aspect, the invention provides a method for determining the pH of a region of a cell by introducing into the cell a polynucleotide encoding a polypeptide including a first fluorescent protein moiety whose emission intensity changes as the pH varies between 5 and 10, culturing the cell under conditions that permit expression of the polynucleotide, and determining the intensity at a first wavelength. The emission intensity of the first fluorescent protein moiety indicates the pH of the sample.

In a further aspect, the invention provides a functional engineered fluorescent protein whose amino acid sequence is substantially identical to the amino acid sequence of the 238 amino acid *Aequorea victoria* green fluorescence protein shown in FIG. 3 of U.S. Ser. No. 08/911,825 (SEQ ID NO: 2), and whose emission intensity changes as pH varies between 5 and 10.

In another aspect, the invention provides a polynucleotide encoding the functional engineered fluorescent protein.

The invention also includes a kit useful for the detection of pH in a sample, e.g., a region of a cell. The kit includes a carrier means containing one or more containers comprising a first container containing a polynucleotide encoding a polypeptide including a first fluorescent protein moiety whose emission intensity changes as the pH varies between 5 and 10.

BRIEF DESCRIPTION OF THE DRAWINGS

FIG. 3A is a graph showing single-wave fluorescence intensities of GT-EYFP and GT-ECFP in the Golgi region of a HeLa cell. FIG. 3B is a graph showing the ratio of GT-EYFP/GT-ECFP fluorescence in the same cell as a function of time.

DETAILED DESCRIPTION

Figure 1:
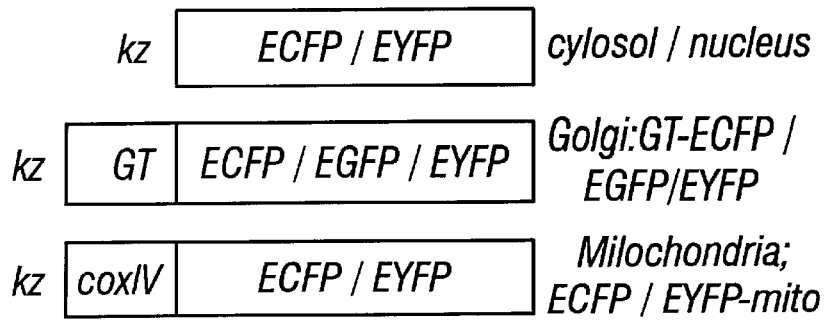
FIG. 1 is a schematic diagram depicting fluorescent protein sensors used as indicators of intracellular pH.

The invention provides genes encoding fluorescent sensor proteins, or fragments thereof, whose fluorescence is sensitive to changes in pH at a range between 5 and 10. The proteins of the invention are useful for measuring the pH of a sample. The sample can be a biological sample and can include an intracellular region of a cell, such as the lumen of the mitochondria or golgi. The pH of a sample is determined by observing the fluorescence of the fluorescent sensor protein.

The fluorescent protein pH sensor have a broad applicability to cells and organisms that are amenable to gene transfer. Problems associated with the use of other agents used to measure pH, e.g., problems associated with permeabilizing cells to ester-containing agents, leakage of agents, or hydrolysis of agents are avoided. With the fluorescent protein pH sensors of the invention, no leakage occurs over the course of a typical measurement, even when the measurement is made at 37° C.

Compositions and methods described herein also avoid the need to express and purify large quantities of soluble recombinant protein, purify and label it in vitro, microinject it back into cells. An important advantage of the fluorescent protein pH sensors of the invention is they can be delivered to cells in the form of polynucleotides encoding the protein sensor fused to a targeting signal or signals. The targeting signal directs the expression of the protein sensors to restricted cell locations. Thus, it is possible to measure the pH of a precisely defined cellular region or organelle.

Polynucleotides and Polypeptides

In a first aspect, the invention provides a functional engineered fluorescent protein whose amino acid sequence is substantially identical to the 238 amino acid *Aequorea victoria* green fluorescence protein shown in FIG. 3 of U.S. Ser. No. 08/911,825 (SEQ ID NO: 2). The term "fluorescent protein" refers to any protein capable of emitting light when excited with appropriate electromagnetic radiation, and which has an amino acid sequence that is either natural or engineered and is derived from the amino acid sequence of Aequorea-related fluorescent protein. The term "fluorescent protein pH sensor" refers to a fluorescent protein whose emitted light varies with changes in pH from 5 to 10.

The invention also includes functional polypeptide fragments of a fluorescent protein pH sensor. As used herein, the term "functional polypeptide fragment" refers to a polypeptide which possesses biological function or activity which is identified through a defined functional assay and which is associated with a particular biologic, morphologic, or phenotypic alteration in the cell. The term "functional fragments of a functional engineered fluorescent protein" refers to fragments of a functional engineered protein that retain a function of the engineered fluorescent protein, e.g., the ability to fluoresce in a pH-dependent manner over the pH range 5 to 10. Biologically functional fragments can vary in size from a polypeptide fragment as small as an epitope to a large polypeptide.

Minor modifications of the functional engineered fluorescent protein may result in proteins which have substantially equivalent activity as compared to the unmodified counterpart polypeptide as described herein. Such modifications may be deliberate, as by site-directed mutagenesis, or may be spontaneous. All of the polypeptides produced by these modifications are included herein as long as the pH-dependent fluorescence of the engineered protein still exists.

A functional engineered fluorescent protein includes amino acid sequences substantially the same as the sequence set forth in SEQ ID NO: 2, and whose emission intensity changes as pH varies between 5 and 10. In some embodiments the emission intensity of the functional engineered fluorescent protein changes as pH varies between 5 and 8.5.

By "substantially identical" is meant a protein or polypeptide that retains the activity of a functional engineered protein, or nucleic acid encoding the same, and which exhibits at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 85%, more preferably 90%, more preferably 95%, more preferably 98%, and most preferably 99% identical at the amino acid level to one of the sequences of EGFP (SEQ ID NO: 4), EYFP (SEQ ID NO: 6), ECFP (SEQ ID NO: 8), or EYFP-V68L/Q69K (SEQ ID NO: 10).

Homology is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various insertions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

In some embodiments, the amino acid sequence of the protein includes one of the following sets of substitutions in the amino acid sequence of the Aequorea green fluorescent protein (SEQ ID NO: 2): F64L/S65T/H231L, referred to herein as EGFP (SEQ ID NO: 4); S65G/S72A/T203Y/H231L, referred to herein as EYFP (SEQ ID NO: 6); S65G/V68L/Q69K/S72A/T203Y/H231L, referred to herein as EYFP-V68L/Q69K (SEQ ID NO: 10); or K26R/F64L/S65T/Y66W/N146I/M153T/V163A/N164H/H231L, referred to herein as ECFP (SEQ ID NO: 8). The DNA sequences and corresponding amino acid sequences of EGFP, EYFP, ECFP, and EYFP-V68L/Q69K are shown in Tables 1–8, respectively. The amino acids are numbered with the amino acid following the iniating methionine assigned the '1' position. Thus, F64L corresponds to a substitution of leucine for phenylalanine in the 64th amino acid following the iniating methionine.

TABLE 1

EGFP Nucleic Acid Sequence (SEQ ID NO:3)

ATGGTGAGCAAGGGCGAGGAGCTGTTCACCGGGGTGGTGCCCATCCTGGTCGAGCTGGAC
GGCGACGTAAACGGCCACAGGTTCAGCGTGTCCGGCGAGGGCGAGGGCGATGCCACCTAC
GGCAAGCTGACCCTGAAGTTCATCTGCACCACCGGCAAGCTGCCCGTGCCCTGGCCCACC
CTCGTGACCACCCTGACCTACGGCGTGCAGTGCTTCAGCCGCTACCCCGACCACATGAAG
CAGCACGACTTCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCAC
AAGCTGGAGTACAACTACAACAGCCACAACGTCTATATCATGGCCGACAAGCAGAAGAAC
GGCATCAAGGTGAACTTCAAGATCCGCCACAACATCGAGGACGGCAGCGTGCAGCTCGCC
GACCACTACCAGCAGAACACCCCCATCGGCGACGGCCCCGTGCTGCTGCCCGACAACCAC
TACCTGAGCACCCAGTCCGCCCTGAGCAAAGACCCCAACGAGAAGCGCGATCACATGGTC
CTGCTGGAGTTCGTGACCGCCGCCGGGATCACTCTCGGCATGGACGAGCTGTACAAGTAA

TABLE 2

EGFP Amino Acid Sequence (SEQ ID NO:4)

MVSKGEELFTGVVPILVELDGDVNGHRFSVSGEGEGDATYGKLTLKFICTTGKLPVPWPT
LVTTLTYGVQCFSRYPDHMKQHDFFKSAMPEGYVQERTIFFKDDGNYKTRAEVKFEGDTL
VNRIELKGIDFKEDGNILGHKLEYNYNSHNVYIMADKQKNGIKVNFKIRHNIEDGSVQLA
DHYQQNTPIGDGPVLLPDNHYLSTQSALSKDPNEKRDHMVLLEFVTAAGITLGMDELYK*

TABLE 3

EYFP Nucleic Acid Sequence (SEQ ID NO:5)

ATGGTGAGCAAGGGCGAGGAGCTGTTCACCGGGGTGGTGCCCATCCTGGTCGAGCTGGAC
GGCGACGTAAACGGCCACAGGTTCAGCGTGTCCGGCGAGGGCGAGGGCGATGCCACCTAC
GGCAAGCTGACCCTGAAGTTCATCTGCACCACCGGCAAGCTGCCCGTGCCCTGGCCCACC
CTCGTGACCACCTTCGGCTACGGCGTGCAGTGCTTCGCCCGCTACCCCGACCACATGAAG
CAGCACGACTTCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCAC
AAGCTGGAGTACAACTACAACAGCCACAACGTCTATATCATGGCCGACAAGCAGAAGAAC
GGCATCAAGGTGAACTTCAAGATCCGCCACAACATCGAGGACGGCAGCGTGCAGCTCGCC
GACCACTACCAGCAGAACACCCCCATCGGCGACGGCCCCGTGCTGCTGCCCGACAACCAC
TACCTGAGCTACCAGTCCGCCCTGAGCAAAGACCCCAACGAGAAGCGCGATCACATGGTC
CTGCTGGAGTTCGTGACCGCCGCCGGGATCACTCTCGGCATGGACGAGCTGTACAAGTAA

TABLE 4

EYFP Amino Acid Sequence (SEQ ID NO:6)

MVSKGEELFTGVVPILVELDGDVNGHRFSVSGEGEGDATYGKLTLKFICTTGKLPVPWPT
LVTTFGYGVQCFARYPDHMKQHDFFKSAMPEGYVQERTIFFKDDGNYKTRAEVKFEGDTL
VNRIELKGIDFKEDGNILGHKLEYNYNSHNVYIMADKQKNGIKVNFKIRHNIEDGSVQLA
DHYQQNTPIGDGPVLLPDNHYLSYQSALSKDPNEKRDHMVLLEFVTAAGITLGMDELYK*

TABLE 5

ECFP Nucleic Acid Sequence (SEQ ID NO:7)

ATGGTGAGCAAGGGCGAGGAGCTGTTCACCGGGGTGGTGCCCATCCTGGTCGAGCTGGAC
GGCGACGTAAACGGCCACAGGTTCAGCGTGTCCGGCGAGGGCGAGGGCGATGCCACCTAC
GGCAAGCTGACCCTGAAGTTCATCTGCACCACCGGCAAGCTGCCCGTGCCCTGGCCCACC
CTCGTGACCACCCTGACCTGGGGCGTGCAGTGCTTCAGCCGCTACCCCGACCACATGAAG
CAGCACGACTTCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCAC
AAGCTGGAGTACAACTACATCAGCCACAACGTCTATATCACCGCCGACAAGCAGAAGAAC
GGCATCAAGGCCCACTTCAAGATCCGCCACAACATCGAGGACGGCAGCGTGCAGCTCGCC
GACCACTACCAGCAGAACACCCCCATCGGCGACGGCCCCGTGCTGCTGCCCGACAACCAC

TABLE 5-continued

ECFP Nucleic Acid Sequence (SEQ ID NO:7)

TACCTGAGCACCCAGTCCGCCCTGAGCAAAGACCCCAACGAGAAGCGCGATCACATGGTC
CTGCTGGAGTTCGTGACCGCCGCCGGGATCACTCTCGGCATGGACGAGCTGTACAAGTAA

TABLE 6

ECFP Amino Acid Sequence (SEQ ID NO:8)

MVSKGEELFTGVVPILVELDGDVNGHRFSVSGEGEGDATYGKLTLKFICTTGKLPVPWPT
LVTTLTWGVQCFSRYPDHMKQHDFFKSAMPEGYVQERTIFFKDDGNYKTRAEVKFEGDTL
VNRIELKGIDFKEDGNILGHKLEYNYISHNVYITADKQKNGIKAHFKIRHNIEDGSVQLA
DHYQQNTPIGDGPVLLPDNHYLSTQSALSKDPNEKRDHMVLLEFVTAAGITLGMDELYK*

TABLE 7

EYFP-V68L/Q69K Nucleic Acid Sequence (SEQ ID NO:9)

ATGGTGAGCAAGGGCGAGGAGCTGTTCACCGGGGTGGTGCCCATCCTGGTCGAGCTGGAC
GGCGACGTAAACGGCCACAGGTTCAGCGTGTCCGGCGAGGGCGAGGGCGATGCCACCTAC
GGCAAGCTGACCCTGAAGTTCATCTGCACCACCGGCAAGCTGCCCGTGCCCTGGCCCACC
CTCGTGACCACCTTCGGCTACGGCCTGAAGTGCTTCGCCCGCTACCCCGACCACATGAAG
CAGCACGACTTCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCAC
AAGCTGGAGTACAACTACAACAGCCACAACGTCTATATCATGGCCGACAAGCAGAAGAAC
GGCATCAAGGTGAACTTCAAGATCCGCCACAACATCGAGGACGGCAGCGTGCAGCTCGCC
GACCACTACCAGCAGAACACCCCCATCGGCGACGGCCCCGTGCTGCTGCCCGACAACCAC
TACCTGAGCTACCAGTCCGCCCTGAGCAAAGACCCCAACGAGAAGCGCGATCACATGGTC
CTGCTGGAGTTCGTGACCGCCGCCGGGATCACTCTCGGCATGGACGAGCTGTACAAGTAA

TABLE 8

EYFP-V68L/Q69K Amino Acid Sequence

MVSKGEELFTGVVPILVELDGDVNGHRFSVSGEGEGDATYGKLTLKFICTTGKLPVPWPT
LVTTFGYGLKCFARYPDHMKQHDFFKSAMPEGYVQERTIFFKDDGNYKTRAEVKFEGDTL
VNRIELKGIDFKEDGNILGHKLEYNYNSHNVYIMADKQKNGIKVNFKIRHNIEDGSVQLA
DHYQQNTPIGDGPVLLPDNHYLSYQSALSKDPNEKRDHMVLLEFVTAAGITLGMDELYK*

In some embodiments, the protein or polypeptide is substantially purified. By "substantially pure protein or polypeptide" is meant an functional engineered fluorescent polypeptide which has been separated from components which naturally accompany it. Typically, the protein or polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, of the protein. A substantially pure protein may be obtained, for example, by extraction from a natural source (e.g., a plant cell); by expression of a recombinant nucleic acid encoding a functional engineered fluorescent protein; or by chemically synthesizing the protein. Purity can be measured by any appropriate method, e.g., those described in column chromatography, polyacrylamide gel electrophoresis, or by HPLC analysis.

A protein or polypeptide is substantially free of naturally associated components when it is separated from those contaminants which accompany it in its natural state. Thus, a protein or polypeptide which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

The invention also provides polynucleotides encoding the functional engineered fluorescent protein described herein. These polynucleotides include DNA, cDNA, and RNA sequences which encode functional engineered fluorescent proteins. It is understood that all polynucleotides encoding functional engineered fluorescent proteins are also included herein, as long as they encode a protein or polypeptide whose fluorescent emission intensity changes as pH varies between 5 and 10. Such polynucleotides include naturally occurring, synthetic, and intentionally manipulated polynucleotides. For example, the polynucleotide may be subjected to site-directed mutagenesis. The polynucleotides of the invention include sequences that are degenerate as a result of the genetic code. Therefore, all degenerate nucleotide sequences are included in the invention as long as the amino acid sequence of the functional engineered fluorescent protein or derivative is functionally unchanged.

Specifically disclosed herein is a polynucleotide sequence encoding a functional engineered fluorescent protein that includes one of the following sets of substitutions in the amino acid sequence of the Aequorea green fluorescent protein (SEQ ID NO: 2): S65G/S72A/T203Y/H231L, S65G/V68L/Q69K/S72A/T203Y/$H_{231}$L, or K26R/F64L/S65T/Y66W/N146I/M153T/V163A/N164H/H231L.

The term "polynucleotide" refers to a polymeric form of nucleotides of at least 10 bases in length. The nucleotides can be ribonucleotides, deoxynucleotides, or modified forms of either type of nucleotide. The term includes single and double stranded forms of DNA. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

A "substantially identical" nucleic acid sequence codes for a substantially identical amino acid sequence as defined above.

The functional engineered fluorescent protein can also include a targeting sequence to direct the fluorescent protein to particular cellular sites by fusion to appropriate organellar targeting signals or localized host proteins. A polynucleotide encoding a targeting sequence can be ligated to the 5' terminus of a polynucleotide encoding the fluorescence such that the targeting peptide is located at the amino terminal end of the resulting fusion polynucleotide/polypeptide. The targeting sequence can be, e.g., a signal peptide. In the case of eukaryotes, the signal peptide is believed to function to transport the fusion polypeptide across the endoplasmic reticulum. The secretory protein is then transported through the Golgi apparatus, into secretory vesicles and into the extracellular space or, preferably, the external environment. Signal peptides which can be utilized according to the invention include pre-pro peptides which contain a proteolytic enzyme recognition site. Other signal peptides with similar properties to pro-calcitonin described herein are known to those skilled in the art, or can be readily ascertained without undue experimentation.

The targeting sequence can also be a nuclear localization sequence, an endoplasmic reticulum localization sequence, a peroxisome localization sequence, a mitochondrial localization sequence, or a localized protein. Targeting sequences can be targeting sequences which are described, for example, in "Protein Targeting", chapter 35 of Stryer, L., Biochemistry (4th ed.). W.H. Freeman, 1995. The localization sequence can also be a localized protein. Some important targeting sequences include those targeting the nucleus (KKKRK, SEQ ID NO: 15), mitochondrion (the 12 amino terminal acids of the cytochrome c oxidase subunit IV gene, or the amino terminal sequence MLRTSSLFTRRVQPSLFRNILRLQST-, SEQ ID NO: 16), endoplasmic reticulum (KDEL (SEQ ID NO: 17) at C-terminus, assuming a signal sequence present at N-terminus), peroxisome (SKF at C-terminus), prenylation or insertion into plasma membrane (CaaX, CC, CXC, or CCXX at C-terminus), cytoplasmic side of plasma membrane (fusion to SNAP-25), or the Golgi apparatus (fusion to the amino terminal 81 amino acids of human type II membrane-anchored protein galactosyltransferase, or fusion to furin).

Examples of targeting sequences linked to functional engineered fluorescent proteins include GT-EYFP, GT-ECFP, GT-EGFP, and GT-EYFP-V68L/Q69K, which are targeted to the Golgi apparatus using sequences from the GT protein; and EYFP-mito (SEQ ID NO: 14) and EGFP-mito (SEQ ID NO: 12), which are targeted to the mitochondrial matrix using sequences from the amino terminal region of the cytochrome c oxidase subunit IV gene. The EYFP, ECFP, EGFP, and EYFP-V68L/Q69K amino acid sequences and corresponding polynucleotide sequences are described above. The GT-derived targeting sequence corresponds to the 81 amino terminal amino acids of the human GT sequence. The GT amino acid sequences, and the polynucleotide sequences encoding the GT amino acid sequences, are described in Genbank Accession No. M70427 and Mengle-Gaw et al., Biochem. Biophys. Res. Commun. 176 (3), 1269–1276 (1991).

Polynucleotide sequences encoding EYFP-mito and ECFP-mito, along with their encoded amino acid sequences, are shown in Tables 9–12.

TABLE 9

ECFP-mito Nucleic Acid Sequence (SEQ ID NO:11)

ATGCTGAGCCTGCGCCAGAGCATCCGCTTCTTCAAGCGCAGCGGCATCATGGTGAGCAAG
GGCGAGGAGCTGTTCACCGGGGTGGTGCCCATCCTGGTCGAGCTGGACGGCGACGTAAAC
GGCCACAGGTTCAGCGTGTCCGGCGAGGGCGAGGGCGATGCCACCTACGGCAAGCTGACC
CTGAAGTTCATCTGCACCACCGGCAAGCTGCCCGTGCCCTGGCCCACCCTCGTGACCACC
CTGACCTGGGGCGTGCAGTGCTTCAGCCGCTACCCCGACCACATGAAGCAGCACGACTTC
TTCAAGTCCGCCATGCCCGAAGGCTACGTCCAGGAGCGCACCATCTTCTTCAAGGACGAC
GGCAACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAGTAC
AACTACATCAGCCACAACGTCTATATCACCGCCGACAAGCAGAAGAACGGCATCAAGGCC
CACTTCAAGATCCGCCACAACATCGAGGACGGCAGCGTGCAGCTCGCCGACCACTACCAG
CAGAACACCCCCATCGGCGACGGCCCCGTGCTGCTGCCCGACAACCACTACCTGAGCACC
CAGTCCGCCCTGAGCAAAGACCCCAACGAGAAGCGCGATCACATGGTCCTGCTGGAGTTC
GTGACCGCCGCCGGGATCACTCTCGGCATGGACGAGCTGTACAAGTAA

TABLE 10

ECFP-mito Amino Acid Sequence (SEQ ID NO:12)

MLSLRQSIRFFKRSGIMVSKGEELFTGVVPILVELDGDVNGHRFSVSGEGEGDATYGKLT
LKFICTTGKLPVPWPTLVTTLTWGVQCFSRYPDHMKQHDFFKSAMPEGYVQERTIFFKDD
GNYKTRAEVKFEGDTLVNRIELKGIDFKEDGNILGHKLEYNYISHNVYITADKQKNGIKA

TABLE 10-continued

ECFP-mito Amino Acid Sequence (SEQ ID NO:12)

HFKIRHNIEDGSVQLADHYQQNTPIGDGPVLLPDNHYLSTQSALSKDPNEKRDHMVLLEF
VTAAGITLGMDELYK*

TABLE 11

EYFP-mito Nucleic Acid Sequence (SEQ ID NO:13)

ATGCTGAGCCTGCGCCAGAGCATCCGCTTCTTCAAGCGCAGCGGCATCATGGTGAGCAAG
GGCGAGGAGCTGTTCACCGGGGTGGTGCCCATCCTGGTCGAGCTGGACGGCGACGTAAAC
GGCCACAGGTTCAGCGTGTCCGGCGAGGGCGAGGGCGATGCCACCTACGGCAAGCTGACC
CTGAAGTTCATCTGCACCACCGGCAAGCTGCCCGTGCCCTGGCCCACCCTCGTGACCACC
TTCGGCTACGGCGTGCAGTGCTTCGCCCGCTACCCCGACCACATGAAGCAGCACGACTTC
TTCAAGTCCGCCATGCCCGAAGGCTACGTCCAGGAGCGCACCATCTTCTTCAAGGACGAC
GGCAACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAGTAC
AACTACAACAGCCACAACGTCTATATCATGGCCGACAAGCAGAAGAACGGCATCAAGGTG
AACTTCAAGATCCGCCACAACATCGAGGACGGCAGCGTGCAGCTCGCCGACCACTACCAG
CAGAACACCCCCATCGGCGACGGCCCCGTGCTGCTGCCCGACAACCACTACCTGAGCTAC
CAGTCCGCCCTGAGCAAAGACCCCAACGAGAAGCGCGATCACATGGTCCTGCTGGAGTTC
GTGACCGCCGCCGGGATCACTCTCGGCATGGACGAGCTGTACAAGTAA

TABLE 12

EYFP-mito Amino Acid Sequence (SEQ ID NO:14)

MLSLRQSIRFFKRSGIMVSKGEELFTGVVPILVELDGDVNGHRFSVSGEGEGDATYGKLT
LKFICTTGKLPVPWPTLVTTFGYGVQCFARYPDHMKQHDFFKSAMPEGYVQERTIFFKDD
GNYKTRAEVKFEGDTLVNRIELKGIDFKEDGNILGHKLEYNYNSHNVYIMADKQKNGIKV
NFKIRHNIEDGSVQLADHYQQNTPIGDGPVLLPDNHYLSYQSALSKDPNEKRDHMVLLEF
VTAAGITLGMDELYK*

The fluorescent indicators can be produced as proteins fused to other fluorescent indicators or targeting sequences by recombinant DNA technology. Recombinant production of fluorescent proteins involves expressing nucleic acids having sequences that encode the proteins. Nucleic acids encoding fluorescent proteins can be obtained by methods known in the art. For example, a nucleic acid encoding the protein can be isolated by polymerase chain reaction of cDNA from *A. victoria* using primers based on the DNA sequence of *A. victoria* green fluorescent protein. PCR methods are described in, for example, U.S. Pat. No. 4,683,195; Mullis, et al. Cold Spring Harbor Symp. Quant. Biol. 51:263 (1987), and Erlich, ed., PCR Technology, (Stockton Press, NY, 1989). Mutant versions of fluorescent proteins can be made by site-specific mutagenesis of other acids encoding fluorescent proteins, or by random mutagenesis caused by increasing the error rate of PCR of the original polynucleotide with 0.1 mM $MnCl_2$ and unbalanced nucleotide concentrations. See, e.g., U.S. patent application Ser. No. 08/337,915, filed Nov. 10, 1994 or International application PCT/US95/14692, filed Nov. 10, 1995.

The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used herein, "operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components whose presence can influence expression, and can also include additional components whose presence is advantageous, for example, leader sequences and fusion partner sequences.

As used herein, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989). Transformation of a host cell with recombinant DNA may be carried out by conventional techniques as are well known to those skilled in the art. Where the host is prokaryotic, such as $E.$ $coli$, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982).

Techniques for the isolation and purification of polypeptides of the invention expressed in prokaryotes or eukaryotes may be by any conventional means such as, for example, preparative chromatographic separations and immunological separations such as those involving the use of monoclonal or polyclonal antibodies or antigen.

A variety of host-expression vector systems may be utilized to express fluorescent indicator coding sequence. These include but are not limited to microorganisms such as bacteria transformed with recombinant bacteriophage DNA, plasmid DNA or cosmid DNA expression vectors containing a fluorescent indicator coding sequence; yeast transformed with recombinant yeast expression vectors containing the fluorescent indicator coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a fluorescent indicator coding sequence; insect cell systems infected with recombinant virus expression vectors (e.g., baculovirus) containing a fluorescent indicator coding sequence; or animal cell systems infected with recombinant virus expression vectors (e.g., retroviruses, adenovirus, vaccinia virus) containing a fluorescent indicator coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516–544, 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5 K promoter) may be used. Promoters produced by recombinant DNA or synthetic techniques may also be used to provide for transcription of the inserted fluorescent indicator coding sequence.

In bacterial systems a number of expression vectors may be advantageously selected depending upon the use intended for the fluorescent indicator expressed. For example, when large quantities of the fluorescent indicator are to be produced, vectors which direct the expression of high levels of fusion protein products that are readily purified may be desirable. Those which are engineered to contain a cleavage site to aid in recovering fluorescent indicator are preferred. In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp.516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. D M Glover, IRL Press, Wash., D.C., 1986). Alternatively, vectors may be used which promote integration of foreign DNA sequences into the yeast chromosome.

In cases where plant expression vectors are used, the expression of a fluorescent indicator coding sequence may be driven by any of a number of promoters. For example, viral promoters such as the 35S RNA and 19S RNA promoters of CaMV (Brisson, et al., Nature 310:511–514, 1984), or the coat protein promoter to TMV (Takamatsu, et al., EMBO J. 6:307–311, 1987) may be used; alternatively, plant promoters such as the small subunit of RUBISCO (Coruzzi, et al., 1984, EMBO J. 3:1671–1680; Broglie, et al., Science 224:838–843, 1984); or heat shock promoters, e.g., soybean hsp17.5-E or hsp17.3-B (Gurley, et al., Mol. Cell. Biol. 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421–463, 1988; and Grierson & Corey, Plant Molecular Biology, 2d Ed., Blackie, London, Ch. 7–9, 1988.

An alternative expression system which could be used to express fluorescent indicator is an insect system. In one such system, *Autographa californica* nuclear polyhedrosis virus (AcNPV) is used as a vector to express foreign genes. The virus grows in *Spodoptera frugiperda* cells. The fluorescent indicator coding sequence may be cloned into non-essential regions (for example, the polyhedrin gene) of the virus and placed under control of an AcNPV promoter (for example the polyhedrin promoter). Successful insertion of the fluorescent indicator coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., J. Viol. 46:584, 1983; Smith, U.S. Pat. No. 4,215,051.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and WI38. Primary cell lines, such as neonatal rat myocytes, can also be used.

Mammalian cell systems which utilize recombinant viruses or viral elements to direct expression may be engineered. For example, when using adenovirus expression vectors, the fluorescent indicator coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, Proc. Natl. Acad. Sci. USA, 81: 3655–3659, 1984). Alternatively, the vaccinia virus 7.5K promoter may be used (e.g., see, Mackett, et al., Proc. Natl. Acad. Sci. USA,79: 7415–7419, 1982; Mackett, et al., J. Virol. 49: 857–864, 1984; Panicali, et al., Proc. Natl. Acad. Sci. USA 79: 4927–4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, Proc. Natl. Acad. Sci. USA, 81:6349–6353, 1984). High level expression may also be achieved using inducible promoters, including, but not limited to, the metallothionein IIA promoter and heat shock promoters.

The recombinant nucleic acid can be incorporated into an expression vector including expression control sequences operatively linked to the recombinant nucleic acid. The expression vector can be adapted for function in prokaryotes or eukaryotes by inclusion of appropriate promoters, replication sequences, markers, etc.

DNA sequences encoding the fluorescence indicator polypeptide of the invention can be expressed in vitro or in vivo by DNA transfer into a suitable recombinant host cell. As used herein, "recombinant host cells" are cells in which a vector can be propagated and its DNA expressed. The term also includes any progeny of the subject host cell. It is understood that all progeny may not be identical to the parental cell since there may be mutations that occur during replication. However, such progeny are included when the term "recombinant host cell" is used. Methods of stable transfer, in other words when the foreign DNA is continuously maintained in the host, are known in the art.

The expression vector can be transfected into a host cell for expression of the recombinant nucleic acid. Recombinant host cells can be selected for high levels of expression in order to purify the fluorescent indicator fusion protein. *E. coli* is useful for this purpose. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell taken in vivo from a transgenic animal.

Transgenic Animals

In another embodiment, the invention provides a transgenic non-human animal that expresses a polynucleotide sequence which encodes a fluorescent protein pH sensor.

The "non-human animals" of the invention comprise any non-human animal having a polynucleotide sequence which encodes a fluorescent indicator. Such non-human animals include vertebrates such as rodents, non-human primates, sheep, dog, cow, pig, amphibians, and reptiles. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic, i.e., animals which include the exogenous genetic material within all of their cells in both alleles. 50% of the resulting animals will include the exogenous genetic material within one allele and 25% will include no exogenous genetic material.

Retroviral infection can also be used to introduce transgene into a non-human animal. The developing non-human embryo can be cultured in vitro to the blastocyst stage. During this time, the blastomeres can be targets for retro viral infection (Jaenisch, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al., Proc. Natl. Acad. Sci.

USA 82:6927–6931, 1985; Van der Putten, et al., Proc. Natl. Acad. Sci USA 82:6148–6152, 1985). Transfection is easily and efficiently obtained by culturing the blastomeres on a monolayer of virus-producing cells (Van der Putten, supra; Stewart, et al., EMBO J. 6:383–388, 1987). Alternatively, infection can be performed at a later stage. Virus or virus-producing cells can be injected into the blastocoele (D. Jahner et al., Nature 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (D. Jahner et al., supra). A third type of target cell for transgene introduction is the embryonal stem cell (ES). ES cells are obtained from pre-implantation embryos cultured in vitro and fused with embryos (M. J. Evans et al. Nature 292:154–156, 1981; M. O. Bradley et al., Nature 309: 255–258,1984; Gossler, et al., Proc. Natl. Acad. Sci USA 83: 9065–9069, 1986; and Robertson et al., Nature 322:445–448, 1986). Transgenes can be efficiently introduced into the ES cells by DNA transfection or by retrovirus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468–1474, 1988).

"Transformed" means a cell into which (or into an ancestor of which) has been introduced, by means of recombinant nucleic acid techniques, a heterologous polynucleotide. "Heterologous" refers to a polynucleotide sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode which encodes the fluorescent indicator which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

Detection of pH Using Fluorescent Indicator Proteins

In another embodiment, the invention provides a method for determining the pH of a sample by contacting the sample with an indicator including a first fluorescent protein moiety whose emission intensity changes as pH varies between pH 5 and 10, exciting the indicator, and then determining the intensity of light emitted by the first fluorescent protein moiety at a first wavelength. The emission intensity of the first fluorescent protein moiety indicates the pH of the sample.

The fluorescent protein moiety can be a functional engineered protein substantially identical to the amino acid sequence of Aequorea green fluorescence protein (SEQ ID NO: 2). Preferred green fluorescence proteins include those having a functional engineered fluorescent protein that includes one of the following sets of substitutions in the amino acid sequence of the Aequorea green fluorescent protein (SEQ ID NO: 2): S65G/S72A/T203Y/H231L, S65G/V68L/Q69K/S72A/T203Y/H231L, or K26R/F64L/S65T/Y66W/N146I/M153T/V163A/N164H/H231L.

The sample in which pH is to be measured can be a biological sample, e.g., a biological tissue such as an extracellular matrix, blood or lymphatic tissue, or a cell. The method is particularly suitable for measuring pH in a specific region of the cell, e.g., the cytosol, or an organellar space such as the inner mitochondrial matrix, the lumen of the Golgi, cytosol, the endoplasmic reticulum, the chloroplast lumen, the lumen of lysosome, or the lumen of an endosome.

In some embodiments, the first fluorescent protein moiety is linked to a targeting sequence that directs the fluorescent protein to a desired cellular compartment. Examples of targeting sequences include the amino terminal 81 amino acids of human type II membrane-anchored protein galactosyltransferase for directing the fluorescent indicator protein to the Golgi and the amino terminal 12 amino acids of the presequence of subunit IV of cytochrome c oxidase for directing a fluorescent pH indicator protein to the mitochondrial matrix. The 12 amino acids of the presequence of subunit IV of cytochrome c oxidase may be linked to the pH fluorescent indicator protein through a linker sequence, e.g., Arg-Ser-Gly-Ile (SEQ ID NO: 18).

In another embodiment, the invention provides a method of determining the pH of a region of a cell by introducing into the cell a polynucleotide encoding a polypeptide including an indicator having a first fluorescent protein moiety whose emission intensity changes as pH varies between 5 and 10, culturing the cell under conditions that permit expression of the polynucleotide; exciting the indicator; and determining the intensity of the light emitted by the first protein moiety at a first wavelength. The emission intensity of the first fluorescent protein moiety indicates the pH of the region of the cell in which the indicator is present.

The polynucleotide can be introduced using methods described above. Thus, the method can be used to measure intracellular pH in cells cultured in vitro, e.g., HeLa cells, or alternatively in vivo, e.g., in cells of an animal carrying a transgene encoding a pH-dependent fluorescent indicator protein.

Fluorescence in the sample can be measured using a fluorometer. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample.

The device can include a temperature controller to maintain the sample at a specific temperature while it is being scanned. If desired, a multi-axis translation stage can be used to move a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y. -L., San Diego: Academic Press (1989), pp. 219–243; Turro, N.J., *Modern Molecular Photochemistry*, Menlo Park: Benjamin/Cummings Publishing Col, Inc. (1978), pp. 296–361.

The pH can be analyzed on cells in vivo, or from samples derived from cells transfected with polynucleotides or proteins expressing the pH indicator proteins. Because fluorescent pH indicator proteins can be expressed recombinantly inside a cell, the pH in an intracellular region, e.g., an organelle, or an extracellular region of an organism can be determined simply by determining changes in fluorescence.

Fluorescent protein pH sensors have may vary in their respective $pK_a$, and the differences in $pK_a$ can be used to select the most suitable fluorescent protein sensor most suitable for a particular application. In general, a sensor protein should be used whose $pK_a$ is close to the pH of the sample to be measured. Preferably the $pK_a$ is within 1.5 pH unit of the sample. More preferably the $pK_a$ is within 1 pH unit, and still more preferably the $pK_a$ is within 0.5 pH unit of the sample.

Thus, a fluorescent protein pH sensor having a $pK_a$ of about 7.1, e.g., the EYFP mutant described below, is preferred for determining the pH of cytosolic, Golgi, and mitochondrial matrix pH areas of a cell. For more acidic organelles, a fluorescence sensor protein having a lower $pK_a$, e.g., a $pK_a$ of about 6.1, is preferred.

To minimize artefactually low fluorescence measurements that occur due to cell movement or focusing, the fluorescence of a the fluorescent protein pH sensor can be compared to the fluorescence of a second sensor, e.g., a second fluorescent protein pH sensor, that is also present in the measured sample. The second fluorescent protein pH sensor should have an emission spectra distinct from the first fluorescent protein pH sensor so that the emission spectra of the two sensors can be distinguished. Because experimental conditions such as focusing and cell movement will affect fluorescence of the second sensor as well as the first sensor, comparing the relative fluorescence of the two sensors allows for the normalization of fluorescence.

A convenient method of comparing the samples is to compute the ratio of the fluorescence of the first fluorescent protein pH sensor to that of the second fluorescent protein pH sensor.

Kits

The materials and components described for use in the methods of the invention are ideally suited for the preparation of a kit. Such a kit may comprise a carrier means being compartmentalized to receive one or more container means such as vials, tubes, and the like, each of the container means comprising one of the separate elements to be used in the method. For example, one of the container means may comprise a polynucleotide encoding a fluorescent protein pH sensor. A second container may further comprise fluorescent protein pH sensor. The constituents may be present in liquid or lyophilized form, as desired.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to limit the scope of the invention described in the claims.

EXAMPLES

Example 1

Construction of Fluorescent Protein pH Sensors

Fluorescent protein pH sensors were constructed by engineering site-specific mutations in polynucleotides encoding forms of the *Aequorea victoria* green fluorescent protein (GFP). The starting GFP variant was the polynucleotide encoding the GFP variant EGFP (for enhanced green fluorescent protein). The EGFP variant had the amino acid substitutions F64L/S65T/H231L relative to the wild-type *Aequorea victoria* GFP sequence.

The ECFP (enhanced cyan fluorescent protein) mutant was constructed by altering the EGFP polynucleotide sequence so that it encoded a protein having the amino acid substitutions K26R/F64L/S65T/Y66W/N146I/M153T/V163A/N164H/H231L relative to the wild-type GFP amino acid sequence. A second variant, named EYFP (enhanced yellow fluorescent protein) was constructed by altering the EGFP polynucleotide to encode a protein having the amino acid substitutions S65G/S72A/T203Y/H231L relative to the amino acid sequence of GFP. A third variant, named EYFP-V68L/Q69K, was constructed by altering the EGFP polynucleotide to encode a protein having the amino acid substitutions S65G/V68L/Q69K/S72A/T203Y/H231L relative to the amino acid sequence of GFP.

A HindIII site and Kozak consensus sequence (GCCACCATG) was introduced at the 5' end of the polynucleotide encoding the GFP variants, and an EcoR1 site was added at the 3' end of the gene of each indicator, and the fragments were ultimately ligated into the HindIII/EcoR1 sites of the mammalian expression vector pcDNA3 (Invitrogen). EGFP and EYFP mutant proteins with no targeting signals were used as indicators of pH in the cytosol or nucleus indicators.

To construct fluorescent protein pH sensors to use as pH indicators in the Golgi, polynucleotides encoding the 81 N-terminal amino acids of the type II membrane-anchored protein galactosyltransferase (GT:UDP-galactose-β,1,4-galactosyltransferase. EC 2.4.1.22) ligated to polynucleotides encoding EGFP, ECFP, or EYFP. The polynucleotides encoding the resulting proteins were named GT-EGFP, GT-ECFP, and GT-EYFP, respectively.

Mitochondrial matrix fluorescent protein pH sensors were constructed by attaching polynucleotides encoding 12 amino acids at the amino terminus to the presequence of subunit IV of cytochrome c oxidase (Hutl et al, EMBO J. 4:2061–68 (1985) to a polynucleotide encoding the amino acid sequence Arg-Sea-Gly-Ile (SEQ ID NO: 18), which in turn was ligated to polynucleotides encoding ECFP or EYFP. These constructs were labeled ECFP-mito or EYFP-mito.

The constructs used to examine intracellular pH are summarized in FIG. 1.

Example 2 pH Titration of Fluroescent Sensor Proteins In Vitro

The pH sensitivity of the fluorescence of the proteins ECFP, EGFP, EYFP, GT-EGFP, and GT-EYFP was first examined.

Absorbance spectra were obtained in a Cary 3E spectrophotometer (Varian). For pH titration, a monochromator-equipped fluorometer (Spex Industries, NJ) and a 96-well microplate fluorometer (Cambridge Technology) were used. In the latter case the filters used for excitation were 482±10 (460±18 for ECFP) and for emission were 532±14. Filters were named as the center wavelength ± the half-bandwidth, both in nm. The solutions for cuvette titration contained 125 mM KCl, 20 mM NaCl, 0.5 mM $CaCl_2$, 0.5 mM $MgCl_2$, and 25 mM of one of the following buffers-acetate, Mes, Mops, Hepes, bicine, and Tris.

Figure 2A:
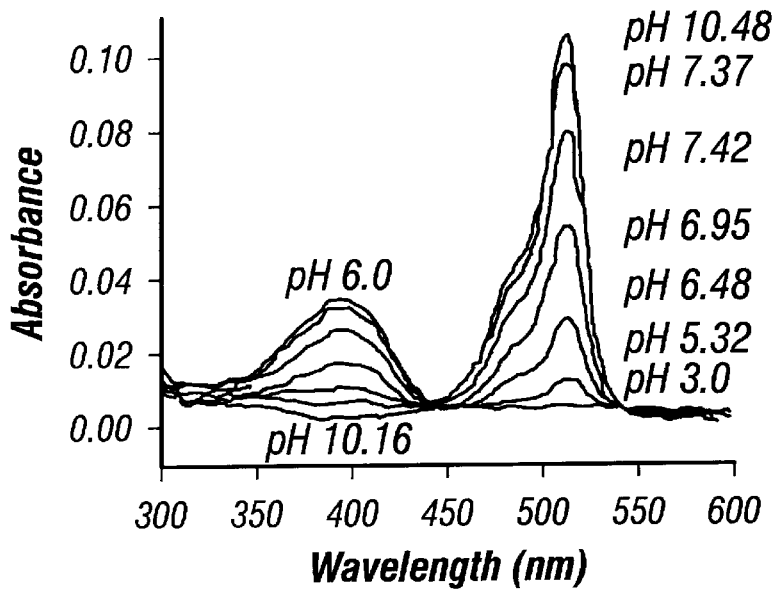
FIGS. 2A and 2B are graphs showing absorbance as a function of wavelength for the fluorescent protein pH sensor EYFP (SEQ ID NO: 6) at various wavelengths (FIG. 2A), and the pH dependency of fluorescence of various GFP fluorescent protein sensors in vitro and in cells (FIG. 2B). The fluorescence intensity of purified recombinant GFP mutant protein (solid symbols) as a function of pH was measured in a microplate fluorometer. The fluorescence of the Golgi region of HeLa cells expressing proteins having the 81 N-terminal amino acids of the type II membrane-anchored protein galactosyltransferase (GT:UDP-galactose-$\beta$,1,4-galactosyltransferase. EC 2.4.1.22) ("GT") fused to EYFP, or EGFP, i.e., GT-EYFP or ET-EGFP (open symbols) was determined during pH titration with the ionophores monensin/nigericin in high KCL solutions.

EYFP showed an acidification-dependent decrease in the absorbance peak at 514 nm and a concomitant increase in absorbance at 390 nm (FIG. 2A). The fluorescence emission (527-nm peak) and excitation spectra decreased with decreasing pH, but the fluorescence excitation spectrum showed no compensating increase at 390 nm. Therefore, the species absorbing at 390 nm was nonfluorescent. The apparent pKa (pK'a) of EYFP was 7.1 with a Hill coefficient (n) of 1.1 (FIG. 2B).

EGFP fluorescence also was quenched with decreasing pH. The pK'a of EGFP was 6.15, and n was 0.7.

Figure 2B:
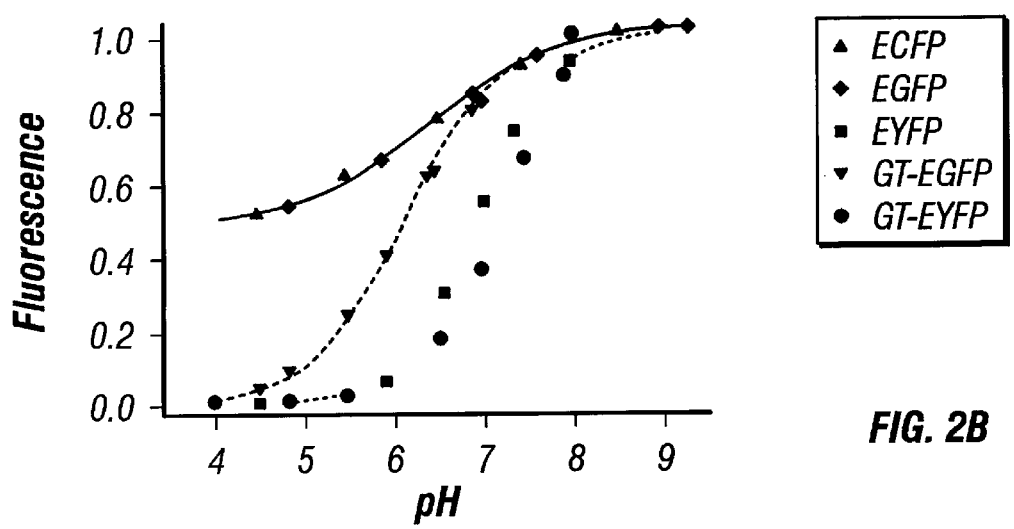

The change in fluorescence of ECFP (Tyr66→Trp in the chromophore) with pH was smaller than that of EGFP or EYFP (pK'a 6.4, n, 0.6) (FIG. 2B). The fluorescence change was reversible in the pH range 5–8.5 for all three proteins, which covers the pH range of most subcellular compartments. These results demonstrate that the GFP variants EGFP, EYFP, and ECFP can be used as fluorescent protein pH sensors.

Example 3

Measurements of pH in the Cytosol and Nucleus Using Fluorescent Protein pH Sensors HeLa cells and AT-20 cells grown on glass coverslips were transiently lipo-transfected (Lipofectin™, GIBCO) with polynucleotide constructs encoding EYFP.

Cells were imaged between 2 and 4 days after transfection at 22° C. with a cooled charge-coupled device camera (Photometrices, Tucson, Ariz.) as described in Miyawaki et al., Nature 388:882, (1997). The interference filters (Omega Optical and Chroma Technology, Brattleboro, Vt.) used for excitation and emission were 440±10 and 480±15 for ECFP; 480±15 and 535±22.5 for EGFP or EYFP. The dichroic mirrors were 455 DCLP for ECFP and 505 DCLP for EGFP or EYFP. Regions of interest were selected manually, and pixel intensities were spatially averaged after background subtraction. A binning of 2 was used to improve signal/noise and minimize photodamage and photoisomerization of EYFP. In the Cl-free bath solution, Na-D gluconate and K-D gluoconate substituted for NaCl and Hanks' balanced salt solution. High KCl buffer plus 5 µM each of the ionophores nigericin (Fluka) and monensin (Calbiochem) was used for in situ titrations in living cells. Cells were loaded with cytosolic pH indicators by incubation with 3 µM carboxy-SNARF/AM or BCECF/AM (Molecular Probes) for 45 minutes, then washed for 30 minutes, all at 22° C.

Fluorescence of HeLa cells transfected with the gene encoding EYFP was diffusely distributed in the cytosol and nucleus. This was expected for a protein of the size of GFP (27 kDa), which is small enough to pass through nuclear pores.

The fluorescence observed with EYFP was reversible. Perfusion with $NH_4Cl$ caused an increase in fluorescence (rise in pH), which reversed upon washing out the $NH_4Cl$. Conversely, perfusion of lactate, which lowers pH, induced a decrease in fluorescence. The decrease in fluorescence was also reversible on wash-out.

Calibration of fluorescence intensity with pH in situ was accomplished with a mix of the alkali cation/H+ ionophores nigericin and monensin in bath solutions of defined pH and high K+. Fluorescence equilibrated within 1–4 minutes after each exchange of solution. These results demonstrate that EYFP, when present intracellularly, can report pH in the physiological range.

Example 4

Measurement of pH in the Mitochondrial Matrix Using Fluorescent Protein pH Sensors To measure pH in the mitochondrial matrix using mutant GFP sensor proteins, HeLa cells and neonatal rat myocytes were transfected with the fluorescent protein pH sensor EYFP-mito. A Bio-Rad MRC-1000 confocal microscope was used for analysis of the targeted protein. Microscopy analysis revealed that the transfected cells showed a fluorescence pattern indistinguishable from that of the conventional mitochondrial dye rhodamine 123.

In situ pH titration was performed with nigericin/monensin as described in Example 3. Subsequent addition of the protonophore carbonylcyanide nt-chlorophenylhydrazone (CCCP) did not change the fluorescence intensity of the cells. This demonstrates that the nigericn/monensin treatment effectively collapsed the pH gradient(ApH)in the mitochondria.

The estimated pHm was 7.98±0.07 in HeLa cells (n=17 cells, from six experiments). Similar pH values were obtained in a HeLa cell line stably expressing EYFP-mito. Resting pH did not change by superfusion of cells with medium 10 mM glucose, which would provide cells with an oxidizable substrate, but 10 mM lactate plus 1 mM pyruvate caused an acidification, which reversed on washout. This can be accounted for by diffusion of protonated acid or by cotransport of pyruvate$^-$/H$^+$ through the inner mitochondrial membrane. The protonophore CCCP rapidly induced an acidification of mitochondria to about pH 7.

Example 5

Measurement of pH in the Golgi Lumen Using Fluorescent Protein pH Sensors

The type II membrane-anchored protein galactosyltransferase (GT:UDP-galactose-β,1,4-galactosyltransferase. EC 2.4.1.22) has been used as a marker of the trans cisternae of the Golgi apparatus (Roth et al., J. Cell Biol. 93:223–29, (1982)). Accordingly, polynucleotide constructs encoding portions of the GT protein fused to the mutant GFP proteins were constructed as described in Example 1 in order to use the GT sequence to target the fluorescent protein pH sensor to the endoplasmic reticulum.

The pH of the Golgi lumen was measured by transfecting HeLa or AT-20 cells with the constructs GT-ECFP, GT-EGFP, or GT-EYFP. Bright juxtanuclear fluorescence was observed, with little increase in diffuse staining above autofluorescence in most cells.

The fluorescence pattern was examined further in double-labeling experiments using rabbit polyclonal α-mannosidase II (α-manII) antibody. Double labeling fluorescence was performed as described by McCaffery et al., Methods Enzymol. 257:259–279 (1995). The α-manII antibody was prepared as described in Velasco et al., J. Cell Biol. 122:39–51 (1993). In the double-staining experiments, it was observed that labeling of the medial trans-Golgi marker α-manII overlapped with GT-EYFP fluorescence.

α-manII was also fused with ECFP, and the pattern of fluorescence obtained upon transfection of the gene was indistinguishable from that of GT-EYFP by light microcopy.

To identify the subcellular localization of GT-EYFP at higher resolution, immunogold electron microscopy was performed on ultra-thin cryosections by using antibodies against GFP. Immunogold labeling of ultra-thin sections was performed as described by McCaffery et al., supra, using rabbit polyclonal anti-GFP antibody or a monoclonal anti-TGN38 antibody.

In double-labeling experiments, GT-EYFP was found in the medial and trans Golgi, although endogenous GT is present in trans Golgi membranes. The difference in localization may occur as a result of overexpression of the GT-EYFP protein.

When protein TGN38 was used as a trans-Golgi network (TGN) marker, its immunogold localization pattern was found to overlap with that of GT-EYFP in the medial/trans-Golgi membranes. The localization data demonstrate that GT-EYFP labels the medial/trans Golgi. Thus, GT-EYFP can be used to identify the pH of this organelle.

The pH titration of GT-EYFP fluorescence in the Golgi region of the cells after treatment with nigericin/monensin was in good agreement with that of EYFP in vitro (see Example 2). Resting pH in HeLa cells was on average 6.58 (range 6.4–6.81, n=30 cells, 9 experiments). These results also demonstrate that neither fusion with GT nor the composition of the Golgi lumen affects the pH sensitivity of EYFP. Thus, Golgi-targeted EYFP can be used as a local pH indicator.

The effect of various treatments on the pH of the Golgi was next examined using Golgi-targeted EYFP.

The pH gradient across the Golgi membrane is maintained by the electrogenic ATP-dependent $H^+$ pump (V-ATPase). The V-ATPase generates a $\Delta pH$ (acidic inside) and $\Delta 104$ (positive inside), which opposes further $H^+$ transport. The movement of counter-ions, $Cl^-$ in (or $K^+$ out), with $H^+$ uptake would shunt the $\Delta \psi$, allowing a larger $\Delta pH$ to be generated. These mechanisms were investigated in intact single HeLa cells transfected with GT-EYFP.

The macrolide antibiotic bafilomycin A1 has been shown to be a potent inhibitor of vacuolar type $H^+$ ATPases (V type). In Hela cells expressing GT-EYFP, bafilomycin A1 (0.2 $\mu M$) increased $pH_G$ by about 0.6 units, to pH 7.16 (range 7.02–7.37, n=12 cells. This suggests that the $H^+$ pump compensates for a positive H+ efflux or leak. The initial rate of Golgi alkalinization by bafilomycin A1 was 0.52 pH units per minute (range 0.3–0.77, n=12 cells), faster than that reported for other acidic compartments such as macrophage phagosomes (0.09 pH/min). Similar results regarding resting pHG and alkalinization by bafilomycin A1 where obtained when HeLa cells were transfected with GT-EGFP. Calibration of GT-EGFP in situ also mirrored its in vitro titration (FIG. 1B). Thus, both EGFP and EYFP are suitable Golgi pH indicators.

Example 6

Measuring Intracellular pH with Two Fluorescent Protein Protein Sensors

Quantitative measurements of fluorescence with nonratiometric indicators can suffer from artifacts as a result of cell movement or focusing. To correct for these effects, the cyan-emitting mutant GT-ECFP was co-transfected into cells along with GT-EYFP. ECFP has excitation and emission peaks that can be separated from those of EYFP by appropriate filters. In addition, ECFP is less pH-sensitive than EYFP (see FIG. 2B).

Figure 3A:
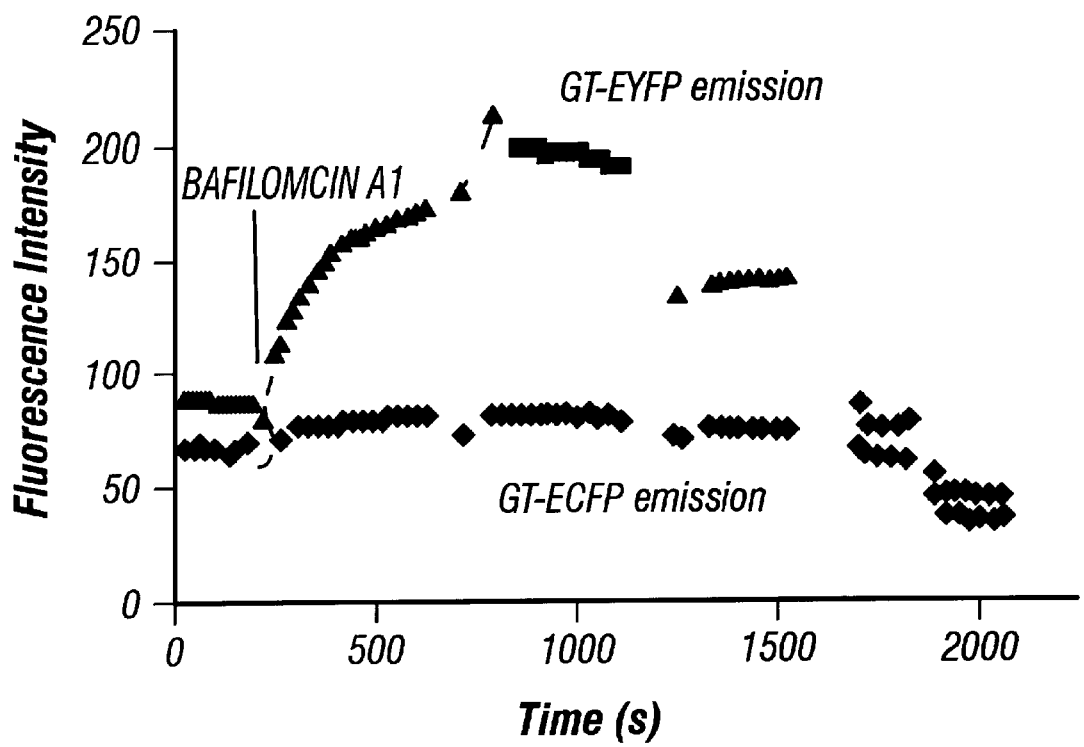
FIGS. 3A and 3B are graphs showing ratiometric measurements of $pH_G$ by cotransfecting HeLa cells with polynucleotides encoding GT-ECFP and GT-EYFP.
Figure 3B:
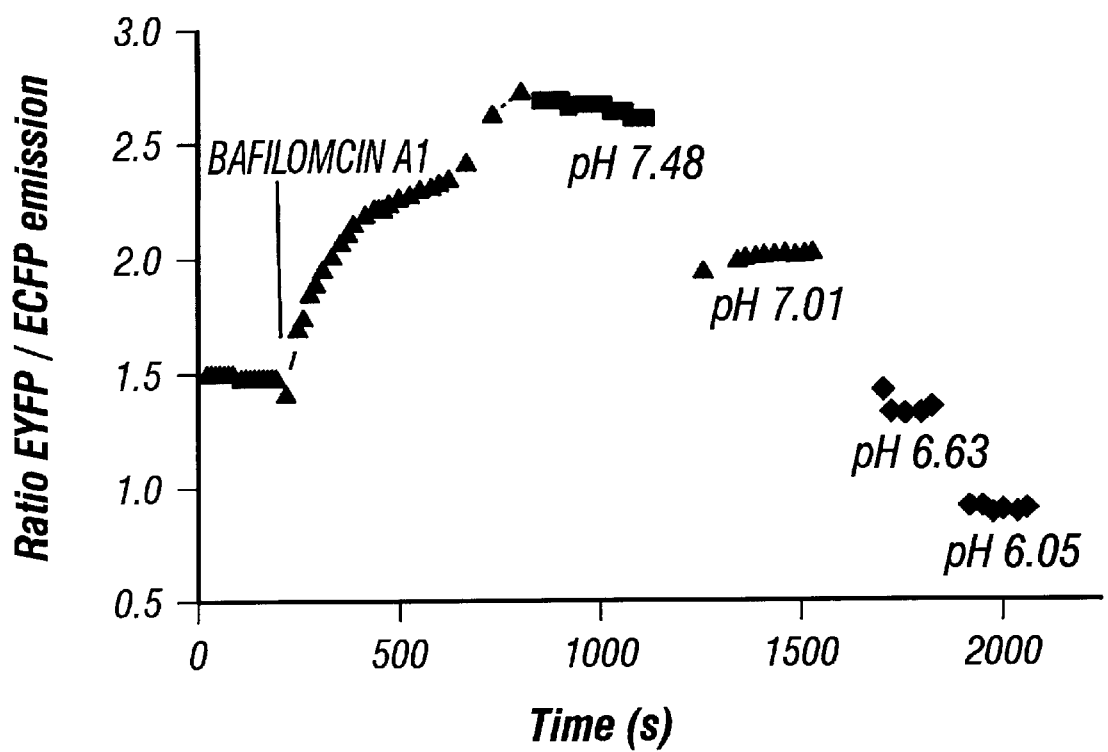

FIG. 3A demonstrates that the fluorescence of ECFP changed less than that of EYFP during the course of the experiment. Although the ratio of EYFP to ECFP emission varied between cells, probably reflecting a different concentration of GT-EYFP and GT-ECFP in the Golgi lumen, it changed with pH as expected (FIG. 3B). Bafilomcin A1 raised the GT-EYFP/GT-ECFP emission ratio, i.e, it raised pHG.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A functional engineered fluorescent protein whose amino acid sequence comprises an amino acid sequence of Aequorea green fluorescent protein (SEQ ID NO: 2) containing substitutions selected from the group consisting of:
    S65G/S72A/T203Y/H231L in SEQ ID NO: 2;
    S65G/V68L/Q69K/S72A/T203Y/H231L in SEQ ID NO: 2; and
    K26R/F64L/S65T/Y66W/N146I/M153T/V163A/N164H/H231L in SEQ ID NO: 2.

2. A method for determining the pH of a sample comprising:
    contacting the sample with an indicator comprising a first fluorescent protein moiety whose emission intensity changes as pH varies between pH 5 and 10, wherein said first fluorescent protein moiety comprises an Aequorea green fluorescent protein (SEQ ID NO: 2) containing substitutions selected from the group consisting of:
    S65G/S72A/T203Y/H231L in SEQ ID NO: 2;
    S65G/V68L/Q69K/S72A/T203Y/H231L in SEQ ID NO: 2; and
    K26R/F64L/S65T/Y66W/N146I/M153T/V163A/N164H/H231L in SEQ ID NO: 2;
    exciting the indicator; and
    determining the intensity of light emitted by the first fluorescent protein moiety at a first wavelength, wherein the emission intensity of the first fluorescent protein moiety indicates the pH of the sample.

3. The method of claim 2, wherein the sample is a biological tissue.

4. The method of claim 2, wherein the sample is a cell or a region thereof.

5. The method of claim 2, further comprising contacting the sample with a second fluorescent protein moiety whose emission intensity changes as pH varies from 5 to 10, wherein the second fluorescent protein moiety emits at a second wavelength that is distinct from the first wavelength and wherein said second fluorescent protein moiety comprises an Aequorea green fluorescent protein (SEQ ID NO:2) containing substitutions selected from the group consisting of:
    S65G/S72A/T203Y/H231L in SEQ ID NO:2;
    S65G/V68L/Q69K/S72A/T203Y/H231L in SEQ ID NO:2; and
    K26R/F64L/S65T/Y66W/N1461I/M153T/V163A/N164H/H231L in SEQ ID NO:2;
    exciting the second protein moiety;
    determining the intensity of light emitted by the second protein moiety at the second wavelength; and
    comparing the fluorescence at the second wavelength to the fluorescence at the first wavelength.

6. The method of claim 2, wherein the first fluorescent protein moiety is linked to a targeting sequence.

7. The method of claim 6, wherein the targeting sequence directs the first fluorescent protein moiety to a region of a cell.

8. The method of claim 7, wherein the region of the cell is the cytosol, the endoplasmic reticulum, the mitochondrial matrix, the chloroplast lumen, the medial trans-Golgi cisternae, the lumen of lysosome, or the lumen of an endosome.

9. The method of claim 8, wherein the targeting sequence comprises the amino terminal 81 amino acids of human type II membrane-anchored protein galactosyltransferase.

10. The method of claim 8, wherein the targeting sequence comprises the amino terminal 12 amino acids of the presequence of subunit IV of cytochrome c oxidase.

11. The method of claim 10, wherein the targeting sequence further comprises the sequence Arg-Ser-Gly-Ile (SEQ ID NO: 18).

12. The method of claim 6, wherein the targeting sequence causes the first fluorescent protein moiety to be secreted from the cell.

13. The method of claim 2, wherein the first fluorescent protein moiety has a pKa greater than 6.1.

14. The method of claim 2, wherein the first fluorescent protein moiety has a pKa greater than 6.3.

15. The method of claim 2, wherein the first fluorescent protein moiety has a pKa greater than 6.9.

16. A kit useful for the detection of the pH in a sample, the kit comprising carrier means containing one or more containers comprising a first container containing a functional engineered fluorescent protein whose amino acid sequence is an amino acid sequence of Aequorea green fluorescent protein (SEQ ID NO: 2) containing substitutions selected from the group consisting of:
    S65G/S72A/H231L in SEQ ID NO: 2;
    S65G/V68L/Q69K/S72A/T203Y/H231L in SEQ ID NO: 2; and
    K26R/F64L/S65T/Y66W/N146I/M153T/V163A/N164H/H231L in SEQ ID NO: 2.

* * * * *